United States Patent [19]
Lyons

[11] Patent Number: 5,524,638
[45] Date of Patent: Jun. 11, 1996

[54] AMUSEMENT DEVICE FOR USE DURING SEXUAL INTERCOURSE

[76] Inventor: Paul Lyons, 295 Elm St., Southridge, Mass. 01550

[21] Appl. No.: 368,745

[22] Filed: Jan. 4, 1995

Related U.S. Application Data

[63] Continuation of Ser. No. 153,470, Nov. 17, 1993, abandoned.

[51] Int. Cl.⁶ .................................................. A61F 6/04
[52] U.S. Cl. ...................... 128/844; 128/883; 446/220
[58] Field of Search ................................ 128/842, 844, 128/883–886; 446/175, 406, 220–226, 404; 604/347–353; 368/276, 82

[56] References Cited

U.S. PATENT DOCUMENTS

| | | | |
|---|---|---|---|
| 494,436 | 3/1893 | Orth | 128/883 |
| 745,264 | 11/1893 | Todd | |
| 4,175,353 | 11/1979 | Pickett | 446/406 |
| 4,365,439 | 12/1982 | Litynski | 446/406 |
| 4,388,000 | 6/1983 | Hagihira | 368/82 |
| 4,639,144 | 1/1987 | Chau | 368/276 |
| 5,163,447 | 11/1992 | Lyons | 128/844 |

FOREIGN PATENT DOCUMENTS

| | | |
|---|---|---|
| 680088 | 10/1952 | United Kingdom . |
| 2036560 | 7/1980 | United Kingdom . |

*Primary Examiner*—Mickey Yu
*Assistant Examiner*—David J. Kenealy
*Attorney, Agent, or Firm*—Wolf, Greenfield & Sacks

[57] ABSTRACT

An amusement device for use during sexual intercourse which can be used alone or with a condom. The device includes a ring portion and a contiguous housing. A circuit is positioned within the housing portion, including at least one sensory unit, such as a sound transducer or a light emitting diode, a power supply source, and an activator.

18 Claims, 2 Drawing Sheets

AMUSEMENT DEVICE FOR USE DURING SEXUAL INTERCOURSE

This application is a continuation of application Ser. No. 08/153,470, filed Nov. 17, 1993 abandoned.

BACKGROUND OF THE INVENTION

1. Field of the Invention

The present invention relates to amusement devices and, more particularly, to sensory amusement devices for use during sexual intercourse which provide entertainment.

2. Description of the Prior Art

Many different kinds of novelty adult amusement devices, used primarily during sexual intercourse or other human sexual activities, exist. Some devices, such as condoms, also provide a means for birth control and disease-prevention. Generally, condoms operate satisfactorily for these purposes, but many persons dislike using them because they reduce sensitivity, interrupt coitus, and are bothersome to wear.

It is therefore an object of this invention to provide a device which can be used with condoms, to encourage condom use by providing entertainment and amusement. It is a further object of the invention to provide a device which can be used without a condom for providing entertainment and amusement during sexual intercourse.

Another object of the invention is to provide a fun gift, which can incorporate at least one sensory unit, such as a sound transducer or a light emitting diode (LED).

SUMMARY OF THE INVENTION

Accordingly, the present invention provides a sensory device for use during sexual intercourse which can be used alone or with a condom. The device includes two primary portions: a ring and a contiguous housing. A circuit is positioned within the housing portion, including at least one sensory unit, such as a sound transducer or an LED, a power supply source, and an activator. In operation, the sensory unit is energized by the power supply in response to activation of the activator.

In one embodiment, the sensory device for use during sexual intercourse can include a plurality of sensory units, such as sound transducers and/or LEDs.

The device operates by applying a predetermined force, which is sufficient to activate the sensory device by, for example, engaging electrical contacts to energize the circuit. The sensory unit will produce sounds, for example, music or a voice message, and/or light flashes (or a series of lights) from an LED(s).

Further advantages and features of the invention will become apparent from a consideration of the ensuing description and drawings.

BRIEF DESCRIPTION OF THE DRAWINGS

The foregoing and other objects and advantages of the invention will be appreciated more fully from the following drawings in which.

DETAILED DESCRIPTION OF THE INVENTION

The present invention provides a novelty adult amusement device. The amusement device for use during sexual intercourse, which can be used alone or with a condom, includes two primary portions: a ring and a housing. Within the device's housing, there are at least one sensory unit, a power source, and an activator. A sensory unit can be any device which can produce sound, light, or any other sensory receptive output, such as a scent.

Figure 1:
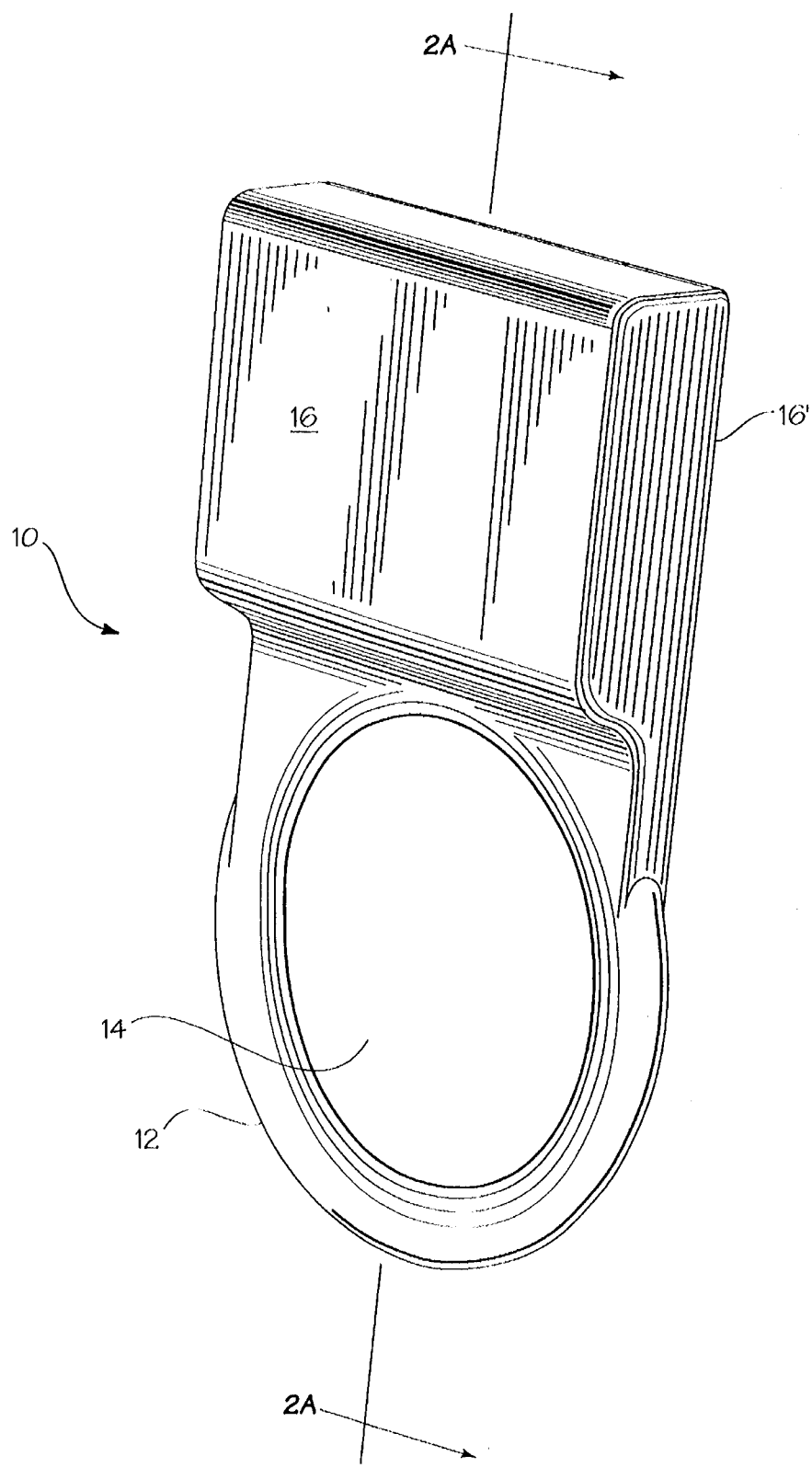
FIG. 1 is a perspective view of the sensory device for use during sexual intercourse of the present invention.
Figure 2A:
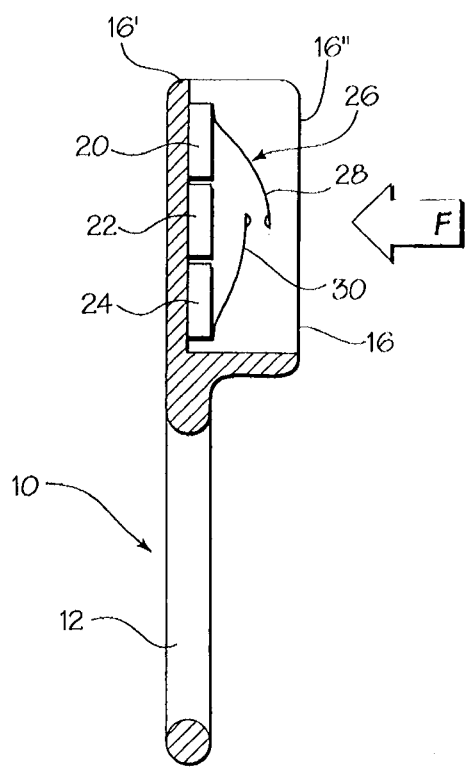
FIG. 2A is a cross-sectional side view of the device, taken along section line 2A—2A of FIG. 1, wherein the sensory unit is a sound transducer.
Figure 2B:
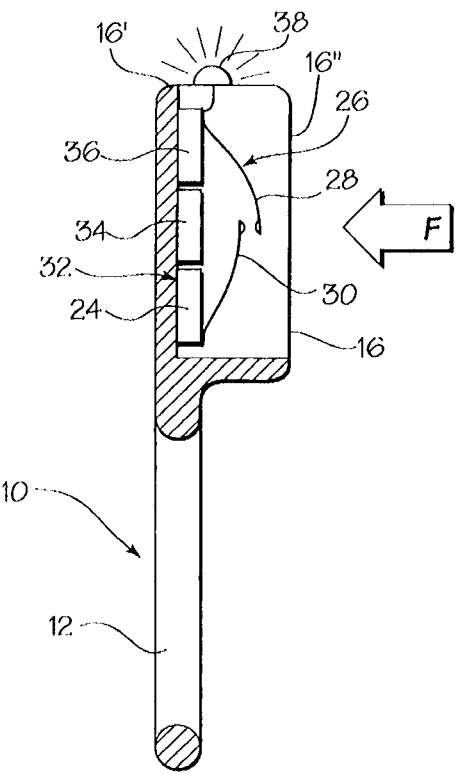
FIG. 2B is a cross-sectional side view of the device, wherein the sensory unit is an LED.

Referring to FIGS. 1, 2A and 2B, a perspective and cross-sectional side views of amusement device 10 are shown. Amusement device 10 includes ring portion 12, forming opening 14, and housing portion 16. Housing 16 extends from one section of ring 12 and supports at least one sensory unit. Ring 12 and housing 16 are typically made from a semi-rigid material, and can be reinforced with a stronger core material. Preferably, ring and housing portions are made from a rubber material, such as latex rubber due to its durability, moldability, softness, and relatively inexpensive raw material and processing costs. Housing 16 includes a solid rear section 16' which is molded integrally with ring 12. Rear section 16' provides a base for positioning a sensory unit and other components, as shown in FIG. 2A. Rear section 16' is upright and coplanar with ring 12.

As shown in FIG. 2A, rear section 16' supports elements of a standard sensory device such as a musical unit, which are known to those skilled in the art (the structure of which is beyond the scope of the present invention). Such a unit usually consists of a miniature piezoelectric sound transducer 20, a microchip 22, which controls the operation of transducer 22, a power-supplying dry-cell battery 24, and a switch, or activator 26, including electrical contacts 28 and 30. As is known to those skilled in the art, when electrical contacts 28 and 30 are closed an appropriate circuit (not shown) from battery 24 to microchip 22 is completed. When energized, microchip 22 will cause transducer 20 to emit a predetermined melody, or voice message. The circuit of microchip 22 also incorporates a monostable multivibrator which controls an electronic bypass switch (not shown) for contacts 28 and 30, and ensures that current will be supplied to microchip 22 for a predetermined period of time (for example, 10 to 15 seconds), so that music continues to play even if contacts 28 and 30 are opened. This will cause the music or voice to play even if contact is intermittent, until the next contact takes place.

The music or voice message may be played once for a predetermined period of time, or it may be repeated continuously for several minutes. Suitable melodies, for example, may be "The 1812 Overture", "The Ode to Joy", "Happy Birthday", "The Anniversary Waltz", "My Ding-A-Ling", "You Light Up My Life", "We've Only Just Begun", "Yellow Submarine", or any popular love song.

As shown in FIG. 2B, amusement device 10 can also include an electrical circuit 32 having a power supply and a flashing circuit, selectively coupled to the power supply, such that when, for example, electrical contacts are closed a circuit is complete and an LED 38 is caused to flash. The circuit 32 utilizes a semiconductor chip 34 which is coupled to battery 24 for powering the device, and a capacitor 36 which can be varied to change the frequency of the output signal on terminals 28 and 30. It is noted that, if desired, additional LEDs may be coupled in parallel with LED 38. The LED 38 can be one commercially available in the art, for example, those designated MT500UR, or Sharp LT-9512U and the like. With regard to the integrated circuit, semiconductor chip 34, those commercially available such as a National Semiconductor 3909 or equivalent, such as a timer designated in the art as a 555 timer, can be used.

In order to protect the amusement device 10, and the above-noted electrical components, from mechanical damage and/or random completion of the circuits through contacts 28 and 30, housing 16 includes protective shield 16". Shield 16" can be made of a semi-rigid rubber or plastic. Preferably, the same material used to form the ring and housing portions, is positioned over the electrical components, and to provide adequate rigidity against sudden engagement of contacts 28 and 30, but also having sufficient elasticity to ensure such contact when a force F is applied to the external surface of shield 16". A force F sufficient to bring contacts 28 and 30 into engagement can be generated with about 5 and about 10 g. Although shown in a rectangular-solid shape, housing 16, and shield 16", can be any shape and size to adequately house the required electrical components. A typical sound or flash-producing unit suitable for the purposes of the present invention may have overall dimensions within the range of between about 7 to about 20 mm.

In operation, the amusement device 10 is placed on the user's penis through opening 14. During sexual intercourse, or other activity, the contact between the suprapubic genital areas of a couple will create forces F sufficient to engage contacts 28 and 30, completing the electrical circuit. Power will pass from battery 24 to chip 22 (or 34), and will cause transducer 20 to produce sounds and/or LED 38 to flash. Moreover, it is understood by those skilled in the art that a combination of sensory devices, for example providing sound and flashing light, can be coupled to provide a multisensory device.

Although the amusement device for use during sexual intercourse 10 has been shown and described in the form of two specific embodiments, these embodiments, their parts, materials and configurations have been given only as examples and other modifications of sensory devices for use during sexual intercourse are possible. For example, as noted above, ring 12 and housing 16 can be made in a variety of sizes and shapes, and can be reinforced by wire or the like. Various parts of the musical or flash circuit may assume lateral positions around the ring 12. It is understood by those skilled in the art that all elements are interconnected through an appropriate fine wiring or printed circuit (not shown) mounted on rear section 16'. Additionally, in lieu of electrical contacts 28 and 30, a strain-gauge-type activator, or any other type of activator, known to those skilled in the art may be employed.

Figure 3:
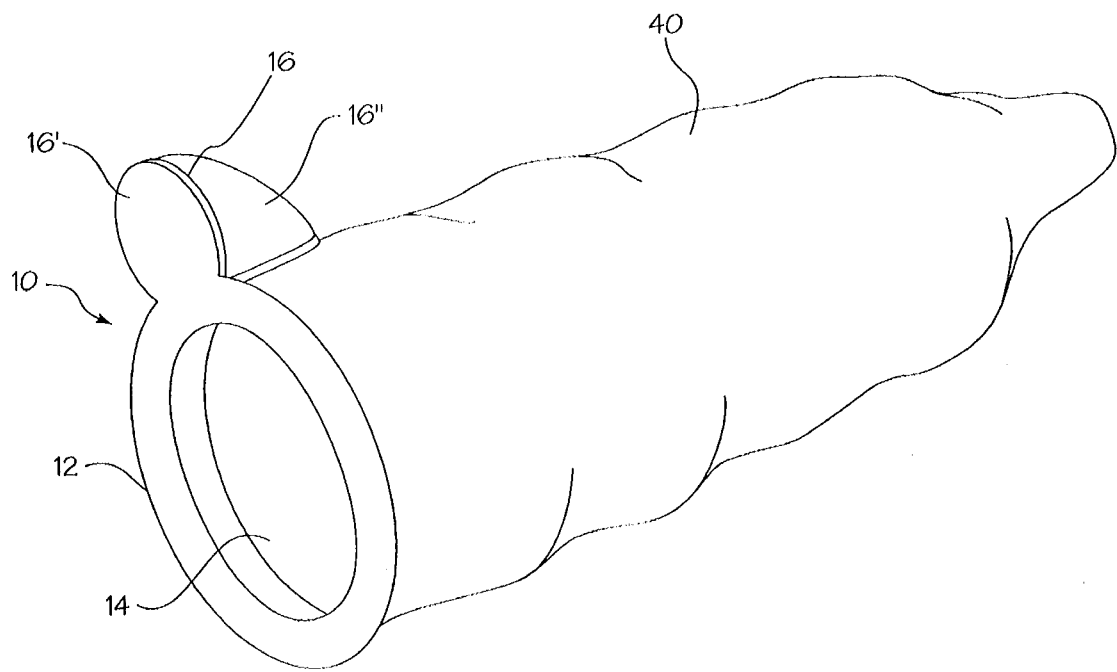
FIG. 3 is a perspective view of the device of the present invention attached to a conventional condom.

As shown in FIG. 3, the amusement device for use during sexual intercourse 10 may be removably attached to a conventional condom body 40 by such means as adhesive tape and the like (not shown).

Although particular embodiments of the invention have been described in detail for purposes of illustration, various modifications may be made without departing from the spirit and scope of the present invention. Accordingly, the invention is not to be limited except as by the appended claims.

What is claimed is:

1. An amusement device for use during sexual intercourse, comprising:

a ring;

a housing which is contiguous with said ring, wherein a circuit is completely enclosed within said housing, said circuit including at least one sensory unit, a power supply source, and an activator; and means for energizing said sensory unit in response to activation of said activator by a force substantially parallel to the central axis of said ring, wherein said ring and housing are made from a latex rubber material.

2. The amusement device of claim 1 wherein said sensory unit is a sound transducer.

3. The amusement device of claim 1 wherein said sensory unit is a light emitting diode.

4. The amusement device of claim 1 wherein said activator includes a pair of force-sensitive electrical contacts.

5. The amusement device of claim 4 wherein said electrical contacts are engaged when a force is generated with at least between about 5 and about 10 grams applied to said housing.

6. The amusement device of claim 1 wherein said circuit further includes a semiconductor chip for use in a flash circuit.

7. The amusement device of claim 1 wherein said housing includes a rear section which is molded integrally with said ring.

8. The amusement device of claim 7, wherein said housing rear section is upright and coplanar with said ring.

9. The amusement device of claim 7, wherein said housing further includes a protective shield.

10. An amusement device for use during sexual intercourse, comprising:

a ring;

a housing which is contiguous with said ring, wherein a circuit is completely enclosed within said housing, said circuit including at least one sensory unit, a power supply source, and an activator; and means for energizing said sensory unit in response to activation of said activator by a force substantially parallel to the central axis of said ring, wherein said ring and housing are made from a semi-rigid material, and said ring is removably attached to a condom.

11. The amusement device of claim 10, wherein said sensory unit is a sound transducer.

12. The amusement device of claim 10, wherein said sensory unit is a light emitting diode.

13. The amusement device of claim 10, wherein said activator includes a pair of force-sensitive electrical contacts.

14. The amusement device of claim 13, wherein said electrical contacts are engaged when a force of at least between about 5 and about 10 g is applied.

15. The amusement device of claim 10, wherein said circuit further includes a semiconductor chip for use in a flash circuit.

16. The amusement device of claim 10, wherein said housing includes a rear section which is molded integrally with said ring.

17. The amusement device of claim 16, wherein said housing rear section is upright and coplanar with said ring.

18. The amusement device of claim 16, wherein said housing further includes a protective shield.

\* \* \* \* \*